United States Patent
Sato et al.

(10) Patent No.: US 12,097,302 B2
(45) Date of Patent: Sep. 24, 2024

(54) METHOD FOR PRODUCING A CULTURED CELL SHEET FOR TISSUE REGENERATION

(71) Applicants: CellSeed Inc., Tokyo (JP); TOKAI UNIVERSITY EDUCATIONAL SYSTEM, Tokyo (JP)

(72) Inventors: Masato Sato, Isehara (JP); Chikako Sato, Tokyo (JP); Tomomi Kotoku, Tokyo (JP); Tomoko Kawake, Tokyo (JP)

(73) Assignees: CELLSEED INC., Tokyo (JP); TOKAI UNIVERSITY EDUCATIONAL SYSTEM, Tokyo (JP)

( * ) Notice: Subject to any disclaimer, the term of this patent is extended or adjusted under 35 U.S.C. 154(b) by 0 days.

(21) Appl. No.: 17/729,608

(22) Filed: Apr. 26, 2022

(65) Prior Publication Data
US 2022/0257833 A1    Aug. 18, 2022

Related U.S. Application Data

(62) Division of application No. 15/555,846, filed as application No. PCT/JP2017/031136 on Aug. 30, 2017, now abandoned.

(30) Foreign Application Priority Data

Feb. 24, 2017    (JP) ................. 2017-033924

(51) Int. Cl.
| | | |
|---|---|---|
| C12N 5/077 | (2010.01) | |
| A61L 27/36 | (2006.01) | |
| A61L 27/38 | (2006.01) | |
| C12N 5/0775 | (2010.01) | |

(52) U.S. Cl.
CPC ....... A61L 27/3612 (2013.01); A61L 27/3817 (2013.01); A61L 27/3834 (2013.01); A61L 27/3852 (2013.01); C12N 5/0655 (2013.01); C12N 5/0668 (2013.01); A61L 2430/06 (2013.01); C12N 2533/30 (2013.01)

(58) Field of Classification Search
CPC ............. A61L 27/3612; A61L 27/3817; A61L 27/3834; A61L 27/3852; A61L 2430/06; C12N 5/0655; C12N 2533/30
See application file for complete search history.

(56) References Cited

FOREIGN PATENT DOCUMENTS

| | | |
|---|---|---|
| EP | 1 410 810 A1 | 4/2004 |
| EP | 1 661 580 A1 | 5/2006 |
| EP | 1 857 126 A1 | 11/2007 |
| EP | 2 617 438 A1 | 7/2013 |
| JP | 2003-111831 A | 4/2003 |
| JP | 2003-180819 A | 7/2003 |
| JP | 2004-136096 A | 5/2004 |
| JP | 2004-531297 A | 10/2004 |
| JP | 2005-130838 A | 5/2005 |
| JP | 4666257 B2 | 4/2011 |
| WO | WO 02/062357 A1 | 8/2002 |
| WO | WO 2006/093151 A1 | 9/2006 |
| WO | WO 2012/036246 A1 | 3/2012 |

OTHER PUBLICATIONS

Anonymous. UPCell; CellSeed, pp. 1-8. downloaded from: https://www.cellseed.com/en/business/product/upcell.html on Apr. 13, 2023. (Year: 2023).*
Kanai et al. Cell Sheets Engineering for Esophageal Regenerative Medicine; Annals of Translational Medicine, vol. 2, No. 3, pp. 1-4. (Year: 2014).*
Nakayama et al. Nano-Scale Physical Surface Coating of Temperature-Responsive Polymers Fro Cell Sheet Fabrication; 2014 International Symposium on Micro-NanoMechatronics and Human Science (MHS), Nagoya, Japan, 2014, pp. 1-2, doi: 10.1109/MHS.2014.7006167. (Year: 2014).*
Brittberg et al., "Treatment of Deep Cartilage Defects in the Knee With Autologous Chondrocyte Transplantation", The New England Journal of Medicine, 1994, vol. 331, No. 14, pp. 889-895.
Japanese Office Action for Japanese Application No. 2017-546927, dated Jun. 18, 2019, with an English translation.
Katano et al., "The forefront of joint tissue regeneration: Meniscal regeneration with synovian stem cells," Nippon Jibiinkoka Gakkai Kaiho (2015), vol. 18, pp. 723-727, with partial English translation.

(Continued)

*Primary Examiner* — Jeanette M Lieb
*Assistant Examiner* — Paul C Martin
(74) *Attorney, Agent, or Firm* — Birch, Stewart, Kolasch & Birch, LLP (57) ABSTRACT

Provided is a cell sheet suitable for cartilage repair. The present invention provides a cell sheet for cartilage repair, formed from a culture of cells derived from a cartilage tissue, and the cell sheet is negative for immunostaining using an antibody against type II collagen. The present invention also provides a method for producing a cell sheet for cartilage repair, formed from a culture of cells derived from a cartilage tissue, and the method includes culturing cells derived from a cartilage tissue on a surface of a membrane, where a temperature-responsive polymer is immobilized on the surface, to give the cell sheet. The culturing is stopped before the cell sheet becomes positive for immunostaining using an antibody against type II collagen.

19 Claims, 1 Drawing Sheet

(56) References Cited

OTHER PUBLICATIONS

Maehara et al, "Changes in Cartilage Characteristics by Passage of Polydactyly-Derived Allogenic Chondrocyte Sheets," Journal of the Japanese Society for Regenerative Medicine (Feb. 1, 2017), Additional Issue vol. 16 Suppl., 440, p. 03-064, with English translation.
Maehara et al., "Characterization of polydactyl-derived chondrocyte sheets versus adult chondrocyte sheets for arcticular cartilage repair," Inflammation and Regeneration (2017), vol. 37, No. 22, pp. 2-11.
Nakajima et al., "In cell sheets for regenerative Automated Culture," Innovative R&D, vol. 95 No. 06-07, 2013, pp. 75-81 (22 pages total), with an English translation.
Numasawa et al., "Treatment of Human Mensenchymal Stem Cells with Angiotensin Receptor Blocker Improved Efficiency of Cardiomyogenic Transdifferentiation and Improved Cardiac Function via Angiogenesis," Stem Cells (2011), vol. 29, pp. 1405-1414.
Office Action issued Mar. 12, 2019, in Japanese Patent Application No. 2017-546927.
Office Action issued Sep. 11, 2018, in Japanese Patent Application No. 2017-546927, with English translation.
Taiwanese Office Action and Search Report dated Oct. 15, 2021 for Application No. 106129700 with an English translation.
Taiwanese Office Action dated Jan. 20, 2022 for Application No. 106129700 with an English translation.
Takahashi et al., "Rabbit Xenotransplantation Model for Evaluating Human Chondrocyte Sheets for Articular Cartilage Repair," ORS 2016 Annual Meeting, Abstract (2016) Poster No. 1407.
Kokubo et al., "Characterization of Chondrocyte Sheets Prepared Using a Co-Culture Method with Temperature-Responsive Culture Inserts", Journal of Tissue Engineering and Regenerative Medicine, vol. 10, 2016 (published online Jul. 19, 2013 in Wiley Online Library), pp. 486-495.
Mitani et al., "Potential Utility of Cell Sheets Derived From the Anterior Cruciate Ligament and Synovium Fabricated in Temperature-Responsive Culture Dishes", Journal of Biomedical Materials Research Part A, vol. 102A, No. 9, Sep. 2014 (published online Sep. 30, 2013 in Wiley Online Library), pp. 2927-2933.
Taiwanese Office Action and Search Report for Taiwanese Application No. 106129700, dated Jul. 6, 2023, with an English translation.

* cited by examiner

METHOD FOR PRODUCING A CULTURED CELL SHEET FOR TISSUE REGENERATION

CROSS-REFERENCE TO RELATED APPLICATIONS

This application is a Divisional of copending application Ser. No. 15/555,846, filed on Nov. 14, 2017 (now abandoned), which was filed as PCT International Application No. PCT/JP2017/031136 on Aug. 30, 2017, which claims the benefit under 35 U.S.C. § 119(a) to Patent Application No. 2017-033924, filed in Japan on Feb. 24, 2017, all of which are hereby expressly incorporated by reference into the present application.

TECHNICAL FIELD

The present invention relates to a cell sheet and a method for producing the cell sheet and more specifically relates to a cell sheet for cartilage repair and a method for producing the cell sheet.

BACKGROUND ART

For procedures of locomotory disorders such as osteoarthritis, tissue regeneration engineering is applied to treat cartilage tissues. In the treatment, cultured chondrocytes or a cartilage tissue prepared from chondrocytes is transplanted to an affected area. Various transplant materials have been disclosed.

For example, Non-Patent Document 1 discloses that healthy chondrocytes were cultured and the cultured chondrocytes were injected into the area of a full-thickness cartilage defect (Abstract). Patent Document 1 discloses "a transplant material for transplantation to a particular transplant site, the transplant material including a cell support carrier prepared by antigenicity suppression treatment of a tissue structure that is derived from a body tissue and is of the same type as the particular transplant site, the cell support carrier maintaining the shape of the tissue structure, the cell support carrier supporting cells corresponding to the particular transplant site" (claim 1). Patent Document 2 discloses "an osteochondral transplant material for filling an osteochondral defect, the osteochondral transplant material being prepared by integrating a gel in which chondrocytes or marrow cells are embedded in solubilized atelocollagen, with a β-tricalcium phosphate porous body serving as an enthesis area into a bone for transplantation, in such a way that they form a portion corresponding to the defect in a cartilage for transplantation; and culturing the chondrocytes or marrow cells in the system" (claim 1). Patent Document 3 discloses "a biocompatible implant including a biocompatible scaffold, and at least one tissue fragment that is associated with at least a portion of the scaffold, the tissue fragment containing an effective amount of viable cells capable of migrating from the tissue fragment and of populating the scaffold" (claim 1). Patent Document 4 discloses "a cultured cell sheet, the cultured cell sheet being in close contact with a carrier, having superior adhesiveness to a cartilage tissue or a bone tissue, and expressing phenotype of a cartilage tissue" (claim 1).

CITATION LIST

Patent Literature

[Patent Document 1] JP-A No. 2003-180819
[Patent Document 2] JP-A No. 2003-111831
[Patent Document 3] JP-A No. 2004-136096
[Patent Document 4] WO No. 2006/093151

Non-Patent Literature

[Non-Patent Document 1] Brittberg et al., New England Journal of Medicine, 1994, 331 (14), 889

SUMMARY OF THE INVENTION

Technical Problem

The purpose of the present invention is to provide a novel cell sheet suitable for cartilage repair. The present invention is also intended to provide a method for producing the cell sheet.

Solution to Problem

The inventors of the present invention have found that a cell sheet having particular features is suitable for cartilage repair.

The present invention provides a cell sheet for cartilage repair, wherein the cell sheet is formed from a culture of cells derived from a cartilage tissue, and the cell sheet is negative for immunostaining using an antibody against type II collagen.

The cell sheet may be positive for immunostaining using an antibody against type I collagen.

The cell sheet may be negative for safranin O staining.

The cell sheet may be positive for immunostaining using an antibody against aggrecan.

In the cell sheet, the cells may be derived from a cartilage tissue of a polydactyly animal.

In the cell sheet, the cells may include a mesenchymal stem cell.

The present invention also provides a method for producing a cell sheet for cartilage repair, wherein the cell sheet is formed from a culture of cells derived from a cartilage tissue. The method comprises culturing cells derived from a cartilage tissue on a surface of a membrane, a temperature-responsive polymer being immobilized on the surface, to obtain the cell sheet, and the culturing is stopped before the cell sheet becomes positive for immunostaining using an antibody against type II collagen.

In the production method, the cell sheet may be positive for immunostaining using an antibody against type I collagen when the culturing is stopped.

In the production method, the culturing may be continued until the cell sheet becomes positive for immunostaining using an antibody against aggrecan.

In the production method, the culturing may be stopped before the cell sheet becomes positive for safranin O staining.

In the production method, an amount of the polymer immobilized on the surface may be 0.3 to 5.0 µg/cm$^2$.

In the production method, the membrane may be a pore membrane, and in the culturing, the cells may be in contact with a culture medium on an upper side of the pore membrane and may be in contact with a culture medium on a lower side of the pore membrane through pores in the pore membrane.

In the production method, the culturing may be performed using a cell culture insert.

Advantageous Effects of Invention

The cell sheet of the present invention is suitable for cartilage repair. By the production method of the present invention, a cell sheet suitable for cartilage repair is produced.

DESCRIPTION OF EMBODIMENTS

1. Cell Sheet

A cell sheet of the present invention is for cartilage repair. In other words, the cell sheet of the present invention is suitable for surgical procedures of cartilage tissues, especially for surgical treatment. In the present invention, the cartilage repair includes treatment of a cartilage tissue with inflammation and/or damage, reinforcement of a cartilage tissue, implant of a defect in a cartilage tissue, and regeneration of a cartilage tissue, but is not limited to them. The cell sheet of the present invention may be used for prevention of diseases associated with cartilage tissues. The cell sheet of the present invention may be applied to a cartilage tissue or a bone tissue with a disease, for example. Examples of the disease to which the cell sheet of the present invention is applicable include arthritis, arthropathy, cartilage damage, osteochondral defect, meniscus injury, and/or intervertebral disk degeneration, but are not limited to them.

The cartilage repair by the cell sheet of the present invention may be performed by the following procedure, for example: a cartilage part to be repaired is exposed by surgical treatment, and the cell sheet is applied to the exposed part. The number and size of the cell sheets to be applied can be appropriately determined by a person skilled in the art in consideration of conditions of the part to be treated or the disease type, for example. Preferably, before the application of the cell sheet of the present invention, the subchondral bone may be treated so as to observe bleeding from the subchondral bone. The treatment may be performed by a method known by a person skilled in the art, and can be performed by means of microfracture or drilling, for example. When performed, the treatment further promotes the cartilage repair by the cell sheet of the present invention.

When the cell sheet of the present invention is applied to an affected area, joining by using an adhesive usable in a living body or suturing may be performed. Alternatively, the cell sheet may be simply attached to an affected area without the joining or suturing.

The cell sheet of the present invention is formed from a culture of cells derived from a cartilage tissue. The cell sheet of the present invention is a sheet-like cell culture, and the culture is a culture of cells derived from a cartilage tissue. The cell sheet of the present invention is obtained by artificial in-vitro cultivation and therefore is not a natural product. The cells derived from a cartilage tissue may be a plurality of cells prepared by separating cells contained in a cartilage tissue from a cartilage matrix, for example. The cells derived from a cartilage tissue may be, for example, a plurality of cells collected by the following procedure: a cartilage tissue is treated with an enzyme to release cells in the cartilage tissue from a cartilage matrix; and the released cells are collected by centrifugation.

In the present invention, the cells derived from a cartilage tissue may be derived from a cartilage tissue of a polydactyly animal or may be derived from a cartilage tissue of a polymelia animal. The animal may preferably be a mammal, more preferably a primate, and even more preferably a human. The cartilage tissue may be collected from a tissue obtained at the time of excision of a supernumerary digit, for example. The tissue may, for example, be a part not appearing as white in a roentgenogram, or a part appearing as black where rays pass through. The polydactyly may be any of a distal phalanx type, a middle phalanx type, and a proximal phalanx type. The supernumerary digit may be any digit, and can be a thumb or a little finger, for example. When a collected supernumerary digit (limb) is wart-like and small, all the collected subcutaneous tissue can be used. When the animal is a human, the human may be preferably 5 years old or less, more preferably 3 years old or less, and even more preferably 2 years old or less for more efficient cultivation.

Preferably, the cells derived from a cartilage tissue are not derived from a synovial membrane. In other words, it is preferred that the cell sheet of the present invention not be formed from a culture of cells derived from a synovial membrane or not be formed from a culture of synovial membrane cells.

Examples of the enzyme used in the enzyme treatment include collagenase, caseinase, clostripain, trypsin, hyaluronidase, elastase, pronase, and DISPASE®. Preferably, a combination of such enzymes may be used. Preferred examples of enzyme combination may be a combination of collagenase, caseinase, clostripain, and trypsin. As examples of the enzyme preparation containing the combination, collagenase type I, collagenase type II, collagenase type III, collagenase type IV, and collagenase type V (each available from Wako Pure Chemical Industries, Ltd.) are mentioned, but the enzyme preparation is not limited to them. Another example of the preferred enzyme combination is a combination of collagenase and DISPASE® or thermolysin, for example. As an example of the enzyme preparation containing the combination is Liberase (available from Roche Diagnostics K. K.), but the enzyme preparation is not limited to this. Depending on tissue conditions, a plurality of enzymes may be used to perform the enzyme treatment step by step. For example, the isolation may be performed by treatment with collagenase, caseinase, clostripain, and trypsin in this order. The conditions for the enzyme treatment may be appropriately set by a person skilled in the art depending on the type of an enzyme used and/or the conditions of a cartilage tissue. The enzyme treatment may be performed at, for example, 30 to 50° C., preferably 33 to 45° C., 35 to 40° C. and for, for example, 1 to 12 hours, preferably 3 to 5 hours, and more preferably 4 to 4.5 hours. Enzyme treatment at an excessively high temperature may cause problems such as cell degeneration, a reduction of the number of living cells, lower proliferative capability, and isolation failure. Enzyme treatment at an excessively low temperature may fail to achieve sufficient enzyme activity, and cells cannot be isolated in some cases. When a physical stimulus is applied in the enzyme treatment, cells can be efficiency collected.

The enzyme reaction may be stopped by adding a culture medium containing serum to the cell suspension in which an articular cartilage is treated with an enzyme. After the stop of the enzyme reaction, the cell suspension is separated by centrifugation into cell aggregate and supernatant. As for Liberase, the enzyme reaction may be stopped by washing twice or more times. The centrifugation may be performed in such conditions as to collect cells with a dimension of less than 25 μm, particularly 20 μm or less and 15 μm or more, as many as possible. In order to collect such cells as many as possible, the centrifugation may be performed at, for example, 1,000 rpm or more, 1,500 rpm or more, or 2,000 rpm or more and for, for example, 5 minutes or more, 7 minutes or more, or 10 minutes or more.

The cells derived from a cartilage tissue may be prepared by what is called an outgrowth method. The outgrowth method may comprise a step of finely cutting a collected cartilage tissue and a step of seeding and culturing the finely cut cartilage tissue fragments together with a small amount of a culture medium on a culture dish. By the culturing, proliferated cells are produced from the cartilage tissue fragments. The produced cells are collected by enzyme treatment and centrifugation. The collected cells may be used to produce the cell sheet of the present invention.

In the outgrowth method, when tissue fragments are in contact with the instrument surface in a smaller area, cells can be efficiently collected. Hence, the tissue fragment preferably has a size of 5 mm$^2$ or less, more preferably 2 mm$^2$ or less, and even more preferably 1 mm$^2$ or less. When the tissue fragment that has been used in the outgrowth method in order to prepare cells is reused in the outgrowth method, more cells can be collected from a single tissue fragment. The number of times of the outgrowth method with respect to a single tissue fragment may be preferably 5 times or less, more preferably 3 times or less, and even more preferably twice or less. If the outgrowth method is performed more than 5 times with respect to a single tissue fragment, the resulting cells, especially, the resulting mesenchymal stem cells may have a lower survival rate, and a prepared cell sheet may fail to efficiently repair a cartilage.

The step of finely cutting a cartilage tissue may be performed in a wet condition, for example. The step may be performed by the following procedure, for example: a tissue fragment and a small amount of a culture medium are placed in a 50-ml centrifuge tube; and the tissue fragment is cut by Metzenbaum Scissors, SuperCut Tungsten Carbide 18 cm Long Curve (World Precision Instruments). The smallest possible cartilage tissue fragments are preferably prepared. The culture medium for culturing finely cut cartilage tissue fragments may be appropriately selected by a person skilled in the art, and is preferably DMEM/F12+20% FBS+an antibiotic (hereinafter also referred to as AB). When the adhesion of cells to a culture dish is observed after the start of culturing, the culture medium may preferably be replaced with DMEM/F12+20% FBS+AB+ascorbic acid (hereinafter also referred to as AA). When a culture medium contains ascorbic acid from the start of culturing, cells can be prevented from adhering to a culture dish. The culturing may be performed under typical culture conditions, and may be performed in an incubator at 37° C. with 5% CO2, for example. The culturing may be performed until subconfluent is achieved. The enzyme preparation used to collect the cells produced in the culturing may contain trypsin and EDTA, for example. The centrifugation may be performed as described above.

In the present invention, the cells derived from a cartilage tissue may be subjected to subcultivation and/or extended cultivation before culturing on a pore membrane. In other words, the culture may be a cell culture prepared by subcultivation and/or extended cultivation of the cell. In the present invention, the subcultivation means passaging of cultured cells together with a fresh culture medium before the cells reach subconfluent and the cell growth rate reaches a maximum (or a plateau). The number of times of subcultivation may be such a number as to allow a resulting cell sheet to achieve intended cartilage regeneration or repair capacity, and can be, for example, 1 to 10, particularly 2 to 9, and more particularly 2 to 5.

In the present invention, the cells derived from a cartilage tissue may preferably include mesenchymal stem cells. The cells derived from a cartilage tissue may further contain cells contained in a cartilage tissue in addition to the mesenchymal stem cells. In other words, the cells derived from a cartilage tissue in the present invention may be a cell population of a plurality of cell types including mesenchymal stem cells. Examples of the cells other than the mesenchymal stem cells include chondrocytes and chondroblasts, but are not limited to them. The cell sheet of the present invention is formed from a culture of the cells derived from a cartilage tissue, and thus is more suitable for cartilage repair.

The cell sheet of the present invention may have a thickness of, for example, 5 to 100 μm, preferably 7 to 70 μm, and more preferably 10 to 50 μm. The cell sheet of the present invention may be formed from naturally stratified cells in a proliferative process of cells. In other words, the cell sheet of the present invention is not necessarily a sheet prepared by artificially laminating separately produced two or more cell sheets and continuously culturing the laminate.

The cell sheet of the present invention is negative for immunostaining using an antibody against type II collagen.

The cartilage tissue is positive for type II collagen. On this account, to develop a graft for cartilage repair, it has been generally considered that the graft is required to be positive for type II collagen. The inventors of the present invention have found that a cell sheet exhibiting negative for immunostaining using an antibody against type II collagen is suitable for cartilage repair. The present invention is based on the finding. The cell sheet of the present invention is negative for type II collagen but is suitable for cartilage repair.

In the present invention, the antibody against type II collagen may be a commercially available antibody. Examples of the commercially available antibody include Anti-Human Type II Collagen (Kyowa Pharma Chemical Co., Ltd., F-57), F(ab')2-Goat anti-Mouse IgG(H+L) Cross-Adsorbed Secondary Antibody, Alexa Fluor 488 (Thermo Fisher Scientific Inc., A-11017), and ImmPRESS (trademark) Reagent Anti-Mouse Ig (Vector Laboratories, Inc., MP-7402-50). In the present invention, the immunostaining using an antibody against type II collagen may be performed by a method known by a person skilled in the art.

The cartilage tissue to which the cell sheet of the present invention has been applied may be positive for immunostaining using an antibody against type II collagen. The timing of the immunostaining may be appropriately set by a person skilled in the art, and the immunostaining may be performed, for example, 1 to 8 weeks after transplantation, particularly 2 to 7 weeks, and more particularly 3 to 6 weeks. The antibody used in the immunostaining may be the same as above.

The cell sheet of the present invention may preferably be positive for immunostaining using an antibody against type II collagen after transplantation to an animal. In other words, the cell sheet of the present invention is negative for immunostaining using an antibody against type II collagen before transplantation and may be positive for the same immunostaining after transplantation. The timing of the immunostaining after transplantation can be appropriately set by a person skilled in the art, and the immunostaining can be performed, for example, 1 to 8 weeks after transplantation, particularly 2 to 7 weeks, and more particularly 3 to 6 weeks. The antibody used in the immunostaining can be the same as above.

The cell sheet of the present invention may be preferably positive for immunostaining using an antibody against type I collagen. A cell sheet having the property can be more suitable for cartilage repair. In the present invention, the antibody against type I collagen may be a commercially available antibody. Examples of the commercially available antibody include Goat Anti-Type I Collagen-UNLB (Southern Biotechnology Associates Inc., 1310-01), Donkey anti-Goat IgG(H+L) Cross-Adsorbed Secondary Antibody, Alexa Fluor 546 (Thermo Fisher Scientific Inc., A-11056), and ImmPRESS (trademark) Reagent Anti-Goat Ig (Vector Laboratories, Inc., MP-7405). In the present invention, the immunostaining using an antibody against type I collagen may be performed by a method known by a person skilled in the art.

The cell sheet of the present invention may be preferably negative for safranin O staining. A cell sheet having the property can be more suitable for cartilage repair. The safranin O may be Safranine O (Chroma Gesellschaft Schmidt & Co., 1B463), for example. In the present invention, the safranin O staining may be performed by a method known by a person skilled in the art.

The cartilage tissue is positive for safranin O staining. On this account, to develop a graft for cartilage repair, it has been generally considered that the graft is required to be positive for safranin O staining. The cell sheet of the present invention is negative for safranin O staining but is suitable for cartilage repair.

The cartilage tissue to which the cell sheet of the present invention has been transplanted may be positive for safranin O staining. The timing of the staining may be appropriately set by a person skilled in the art, and the staining can be performed, for example, 1 to 8 weeks after transplantation, particularly 2 to 7 weeks, and more particularly 3 to 6 weeks.

The cell sheet of the present invention may be preferably positive for immunostaining using an antibody against aggrecan. A cell sheet having the property can be more suitable for cartilage repair. In the present invention, the antibody against aggrecan may be a commercially available antibody. Examples of the commercially available antibody include Aggrecan, G1-IGD-G2 Domain, Human, Recombinant, Carrier-free (R&D Systems, Inc., 1220-PG-025) and Donkey anti-Goat IgG(H+L) Cross-Adsorbed Secondary Antibody, Alexa Fluor 546 (Thermo Fisher Scientific Inc., A-11056). In the present invention, the immunostaining using an antibody against aggrecan may be performed by a method known by a person skilled in the art.

In a preferred embodiment, the cell sheet of the present invention may be a cell sheet that is negative for immunostaining using an antibody against type II collagen and is positive for immunostaining using an antibody against type I collagen. In a more preferred embodiment, the cell sheet of the present invention may be a cell sheet that is negative for immunostaining using an antibody against type II collagen, positive for immunostaining using an antibody against type I collagen, and negative for safranin O staining and/or positive for immunostaining using an antibody against aggrecan. When having such features, the cell sheet of the present invention can be more suitable for cartilage repair.

The cell sheet of the present invention may preferably have a matrix on all surfaces of the cell sheet. Preferably, the matrix may contain fibronectin. When cells are cultured on a substrate, a matrix is typically produced between the cells and the substrate, and no matrix is produced on the side opposite to the substrate, or on a part that is not in contact with the substrate. In the cell sheet of the present invention, a matrix can be generated not only on a surface that is in contact with the substrate but also on a surface that is not in contact with the substrate. The cell sheet of the present invention has a matrix on all surfaces on the cell sheet and thus can be more suitable for cartilage repair.

Preferably, in the cell sheet of the present invention, basement membrane-like proteins between the cells and the pore membrane produced during culturing are not destroyed by an enzyme such as a protease including DISPASE® and trypsin. In other words, the cell sheet of the present invention may have basement membrane-like proteins between the cells and the pore membrane. In particular, the cell sheet of the present invention may have basement membrane-like proteins between the cells and the pore membrane, on one surface of the sheet or both surfaces of the sheet. A cell sheet having the basement membrane-like proteins can exert higher cartilage repair capacity.

The cell sheet of the present invention may preferably have a cell density of $100\times10^5$ to $100\times10^8$ cells/cm$^3$, more preferably $100\times10^6$ to $100\times10^7$ cells/cm$^3$, even more preferably $100\times10^6$ to $500\times10^6$ cells/cm$^3$, and further more preferably $200\times10^6$ to $300\times10^6$ cells/cm$^3$.

Even when subjected to allogeneic (homologous) transplantation, the cell sheet of the present invention causes no immune reaction but can contribute to the cartilage repair. Hence, the cell sheet can be subjected to allogeneic (homologous) transplantation. The chondrocytes in the cell sheet cause no immune reaction, and the produced matrix prevents the cell sheet from being recognized as an antigen. These are supposed to help the cell sheet to cause no immune reaction.

The cell sheet of the present invention preferably includes no artificial scaffold component. In other words, the cell sheet of the present invention can consist only of the cells in the culture and components produced from the cells (and culture medium components adhering to the cell sheet). The cell sheet of the present invention can be preferably transplanted with no artificial scaffold component to a patient.

The cell sheet of the present invention may be produced by the production method of the present invention described in section 2 below. The method for producing the cell sheet of the present invention will be described in section 2 below.

2. Method for Producing Cell Sheet

The present invention provides a method for producing a cell sheet for cartilage repair, formed from a culture of cells derived from a cartilage tissue. The method comprises culturing cells derived from a cartilage tissue on a surface of a membrane, where a temperature-responsive polymer is immobilized on the surface, to obtain the cell sheet, and the culturing is stopped before the cell sheet becomes positive for immunostaining using an antibody against type II collagen. In other words, the cell sheet produced by the production method of the present invention is negative for immunostaining using an antibody against type II collagen. By the method, a cell sheet suitable for cartilage repair is produced.

In the production method of the present invention, the cell sheet may be preferably positive for immunostaining using an antibody against type I collagen when the culturing is stopped. In other words, the culturing may be stopped when positive for immunostaining using an antibody against type I collagen is identified. By such culturing, a cell sheet more suitable for cartilage repair can be produced.

In the production method of the present invention, the culturing may preferably be stopped before the cell sheet becomes positive for safranin O staining. By such culturing, a cell sheet more suitable for cartilage repair can be produced.

In the production method of the present invention, the culturing may preferably be continued until the cell sheet becomes positive for immunostaining using an antibody against aggrecan. In other words, the culturing may be stopped after the cell sheet becomes positive for immunostaining using an antibody against aggrecan. By such culturing, a cell sheet more suitable for cartilage repair can be produced.

In the production method of the present invention, the cells derived from a cartilage tissue are cultured on a membrane surface on which a temperature-responsive polymer is immobilized. By culturing the cells on a surface on which a temperature-responsive polymer is immobilized, a resulting culture on the surface can be released without damage after culturing. In other words, by setting the temperature of the culture medium at not less than an upper critical solution temperature of the temperature-responsive polymer or at not more than a lower critical solution temperature after culturing, the surface changes from hydrophobic to hydrophilic, and consequently the culture is easily released from the pore membrane. The culturing in the production method of the present invention is what is called two-dimensional culture (also called flat culture). The two-dimensional culture is not three-dimensional culture such as suspension culture and pellet culture.

In the production method of the present invention, the membrane may be a pore membrane, and in the culturing, the cells may be in contact with a culture medium on an upper side of the pore membrane and may be in contact with a culture medium on a lower side of the pore membrane through pores in the pore membrane. By culturing cells in such conditions, cells more suitable for cartilage repair can be prepared.

To release the cell sheet produced in the production method of the present invention from the pore membrane, treatment with a protease such as DISPASE® and trypsin is unnecessary. By using characteristics of the temperature-responsive polymer and changing the temperature of the culture medium, the cell sheet can be released from the pore membrane. Hence, the cell sheet produced by the production method of the present invention has an advantage of being releasable from a pore membrane without damage by the enzyme.

The treatment with a protease may cause degradation of an intercellular desmosome structure and basement membrane-like proteins between cells and a substrate, and consequently the cells in a released cell sheet may be individually separated. In contrast, the cell sheet produced by the production method of the present invention can be released from a pore membrane by changing the temperature of a culture medium without protease treatment. As a result, the desmosome structure can be maintained, and the cell sheet can have a few structural defects and have higher strength. When the cell sheet produced by the production method of the present invention is released from a pore membrane by changing the temperature of a culture medium, the basement membrane-like proteins are not destroyed by an enzyme. Hence, the cell sheet can more firmly adhere to the tissue of an affected area at the time of transplantation and enables efficient treatment.

It is known that DISPASE® as a protease can release a cell sheet while 10 to 60% of the desmosome structure is maintained but destroys almost all the basement membrane-like proteins, and thus a resulting cell sheet has a low strength.

The cell sheet produced by the production method of the present invention can be released from a pore membrane while maintaining 80% or more of both the desmosome structure and the basement membrane-like proteins.

The upper critical solution temperature or the lower critical solution temperature of the temperature-responsive polymer used in the present invention can be preferably 0° C. to 80° C., more preferably 20° C. to 50° C., and even more preferably 25 to 45° C. If the upper critical solution temperature or the lower critical solution temperature is excessively high, cells may be killed. If the upper critical solution temperature or the lower critical solution temperature is excessively low, the cell proliferation rate can be reduced, or cells may be killed.

In the production method of the present invention, the temperature-responsive polymer may be either a homopolymer or a copolymer. The polymer may be a homopolymer of a (meth)acrylamide compound, an N- (or N,N-di)alkyl-substituted (meth)acrylamide derivative, or a vinyl ether derivative or may be a copolymer of such monomers, for example.

The (meth)acrylamide compound may be acrylamide or methacrylamide, for example.

The N-alkyl-substituted (meth)acrylamide derivative may be N-ethylacrylamide (lower critical solution temperature of a homopolymer: 72° C.), N-n-propylacrylamide (ditto: 21° C.), N-n-propylmethacrylamide (ditto: 27° C.), N-isopropylacrylamide (ditto: 32° C.), N-isopropylmethacrylamide (ditto: 43° C.), N-cyclopropylacrylamide (ditto: 45° C.), N-cyclopropylmethacrylamide (ditto: 60° C.), N-ethoxyethylacrylamide (ditto: about 35° C.), N-ethoxyethylmethacrylamide (ditto: about 45° C.), N-tetrahydrofurfurylacrylamide (ditto: about 28° C.), or N-tetrahydrofurfurylmethacrylamide (ditto: about 35° C.), for example.

The N,N-dialkyl-substituted (meth)acrylamide derivative can be N,N-dimethyl(meth)acrylamide, N, N-ethylmethylacrylamide (lower critical solution temperature of a homopolymer: 56° C.), or N,N-diethylacrylamide (ditto: 32° C.), for example.

The vinyl ether derivative can be methyl vinyl ether (lower critical solution temperature of a homopolymer: 35° C.), for example.

In the present invention, the temperature-responsive polymer can be a copolymer with a monomer other than the above monomers, and a graft polymer of polymers, a copolymer of polymers, a mixture of polymers, or a mixture of copolymers can be used. A polymer may be crosslinked as long as the original characteristics of the polymer are not impaired.

In order to select a temperature-responsive polymer having the critical solution temperature more suitable for culture or release in the present invention, to control the interaction between a pore membrane and a culture, or to control the hydrophilicity or hydrophobicity of a pore membrane surface, the polymer may be appropriately selected.

In a preferred embodiment, the temperature-responsive polymer is poly(N-isopropylacrylamide).

In the production method of the present invention, the amount of the temperature-responsive polymer immobilized on the membrane surface may be preferably 0.3 to 5.0 µg/cm² and more preferably 0.3 to 4.8 µg/cm². When the membrane is a pore membrane, especially when the membrane is a pore membrane and a cell culture insert is used for culturing, the amount of the temperature-responsive polymer immobilized on the membrane surface may be preferably 0.3 to 1.5 µg/cm². When the membrane is not a pore membrane, the amount of the temperature-responsive polymer immobilized on the membrane surface may be preferably 1 to 2 µg/cm². When the immobilized amount of the temperature-responsive polymer is within the range, the culturing can be more efficiently performed than the above. If the immobilized amount is out of the range, no cell sheet may be formed, or the cell sheet may not be efficiently produced. When the immobilized amount is within the range, the cell sheet can be more easily released from the membrane.

In the production method of the present invention, the membrane is preferably a pore membrane, and in the culturing, the cells derived from a cartilage tissue is preferably in contact with a culture medium on the upper side of the pore membrane and is preferably in contact with a culture medium on the lower side of the pore membrane through pores in the pore membrane. By culturing in such conditions, the culturing can be more efficiently performed.

In the production method of the present invention, the material of the membrane, especially, of the pore membrane, may be polycarbonate, polyester, polyethylene terephthalate (PET), polystyrene, or polytetrafluoroethylene, for example. PET is particularly preferred. By using a PET pore membrane, the cell sheet of the present invention can be more efficiently produced.

The temperature-responsive polymer may be immobilized on the pore membrane surface by a method described in JP-A No. 2-211865, for example. In other words, the immobilization can be performed by a method of bonding a temperature-responsive polymer to a pore membrane by chemical reaction or a bonding method by physical interaction. These methods may be used in combination.

In the bonding method by chemical reaction, electron beam irradiation (EB), γ-ray irradiation, ultraviolet irradiation, visible light irradiation, LED irradiation, plasma treatment, or corona treatment may be performed, for example. Alternatively, a commonly used organic reaction such as radical reaction, anion radical reaction, and cation radical reaction can be performed to immobilize the temperature-responsive polymer on the pore membrane. Alternatively, a block copolymer having a structure in which a water-insoluble polymer segment and a temperature-responsive polymer segment are bonded may be applied onto the substrate surface as a temperature-responsive polymer component. Physical adsorption or hydrophobicity may be used for immobilization.

In the bonding method by physical interaction, the temperature-responsive polymer or a mixture of the polymer and any medium may be applied onto a pore membrane.

The culture medium used in the culturing in the production method of the present invention may be a culture medium usable for cell culture, especially for culturing mammalian cells, including DMEM/F12 (Dulbecco's Modified Eagle Medium: Nutrient Mixture F-12). The culture medium can contain an additional factor. As the additional factor, a cell growth factor, a hormone, a binding protein, a cell adhesion molecule, a lipid, and other components may be mentioned.

As the cell growth factor, TGF-β, b-FGF, IGF, EGF (epidermal growth factor), BMP (bone morphogenetic protein), fibroblast growth factor receptor 3 (FGFR-3), frizzled-related protein (FRZB), CDMP-1, growth differentiation factor 5 (GDF-5), G-CSF (granulocyte colony-stimulating factor), LIF (leukemia inhibitory factor), interleukin, PDGF (platelet-derived growth factor), NGF (nerve growth factor), a TGF (transforming growth factor) family such as activin A, and a Wnt family, specifically Wnt-3a (a wingless-type MMTV integration site family, member 3A) are mentioned, but examples of the cell growth factor are not limited to them. The TGF family includes TGF-β1, TGF-β2, and TGF-β3.

As the hormone, insulin, transferrin, dexamethasone, estradiol, prolactin, glucagon, thyroxine, growth hormone, FSH (follicle stimulating hormone), LH (luteinizing hormone), glucocorticoid, and prostaglandin are mentioned, but examples of the hormone are not limited to them.

As the cell adhesion molecule, collagen, collagen-like peptides, fibronectin, laminin, and vitronectin are mentioned, but examples of the cell adhesion molecule are not limited to them. The collagen-like peptide is exemplified by a recombinant peptide in which an RGD sequence-containing region in collagen is connected. An example of such a recombinant peptide is cellnest (Fujifilm Corporation).

As the lipid, phospholipids and unsaturated fatty acids are mentioned, but examples of the lipid are not limited to them.

As the other components capable of being contained in the culture medium, ascorbic acid, serum, insulin transferrin selenite (ITS), transferrin, sodium selenite, pyruvic acid, proline, albumin, lipoprotein, and ceruloplasmin are mentioned, but examples of the components are not limited to them. As the serum, fetal bovine serum (FBS) and human serum are mentioned, but examples of the serum are not limited to them. In the production method of the present invention, the culture medium is preferably a culture medium containing FBS, and especially may be DMEM/F12 containing FBS. For more efficient culturing, the content of FBS may preferably be 1 to 30% by volume, preferably 10 to 30% by volume, more preferably 12 to 28% by volume, and even more preferably 15 to 25% by volume relative to the total volume of the culture medium.

In the production method of the present invention, the culture medium may be a serum free culture medium. The additional factor such as ITS may function as a substitute for serum, and thus a serum free culture medium containing the additional factor may be used to perform the culturing in the production method of the present invention. By using a serum free culture medium, the risk associated with using a biological material can be avoided for transplantation to a human.

Preferably, the culture medium used in the present invention may contain ascorbic acid at a content of, for example, 0.01 to 1 mg/mL, preferably 0.05 to 0.5 mg/mL, and more preferably 0.07 to 0.3 mg/mL relative to the volume of the culture medium for better cell proliferation. Ascorbic acid can help the cultured cells to produce an articular cartilage-specific matrix and/or can allow the cell sheet to express characters more suitable for cartilage repair. In other words, ascorbic acid can contribute to regeneration of a damaged part in an articular cartilage by a hyaline cartilage. If the ascorbic acid concentration is excessively high, the cultured cells can be prevented from adhering to a pore membrane. If the ascorbic acid concentration is excessively low, the effect to be attained by ascorbic acid cannot be exerted in some cases.

In the production method of the present invention, the culture period of cells derived from a cartilage tissue on a membrane may be appropriately set depending on conditions of a culture, including phenotypic expression conditions, and may be, for example, 10 to 20 days, preferably 11 to 18 days, and more preferably 12 to 16 days. By culturing cells for the culture period, a resulting cell sheet can be more suitable for cartilage repair.

The culturing can be performed while the cell population is in contact with a culture medium on the upper side of the pore membrane and is in contact with a culture medium on the lower side of the pore membrane through pores in the pore membrane. By culturing cells in the condition, adhesive proteins can be produced not only on an adhesive surface to the pore membrane of the cell sheet but also on the surface opposite to the adhesive surface, or the surface in contact with the culture medium on the upper side. The cell sheet of the present invention may have a matrix on both sides of the cell sheet, and thus can be more suitable for cartilage repair.

In order to culture cells in the above conditions, a cell insert (also referred to as cell culture insert) or a culture container having a similar structure can be used, for example. A culture container having a cell insert in which a temperature-responsive polymer is immobilized on a pore membrane part may be used in the production method of the present invention, for example. On the pore membrane surface on which a temperature-responsive polymer is immobilized, the cell population may be cultured.

The temperature-responsive polymer may be immobilized by a method known by a person skilled in the art, for example, by a method described in JP-A No. 2-211865. The cell insert on which a temperature-responsive polymer is immobilized may be a commercially available product, and Thermo Scientific (trademark) Nunc (trademark) CC insert #140660 and BD Falcon cell culture insert #353090, #353490, 353102, #353091, #353092, and #353093 may be used.

In the production method of the present invention, the culture container may be appropriately selected by a person skilled in the art. A dish, a multi-well plate, a flask, and containers having a similar shape are mentioned as the culture container, but examples of the culture container are not limited to them.

The features of the cell sheet produced in the production method of the present invention are as described in section 1 above. The cells derived from a cartilage tissue used in the production method of the present invention and the preparation method of the cells are as described in section 1 above.

In the production method of the present invention, the culturing may be performed under conditions employed in common cell culturing. The culturing may be performed in an incubator at, for example, 35 to 40° C., especially 37° C., and with 2 to 8% CO2, specifically 5% CO2.

In the production method of the present invention, hypoxic culturing may be employed. The culturing may be performed in an atmosphere at an oxygen concentration of, for example, less than 20%, preferably 15% or less, more preferably 10% or less, even more preferably 5% or less, and most preferably 2% or less. The oxygen concentration is however required to be more than 0%. By culturing cells at a low-oxygen concentration, the chondrocyte proliferative capability is increased, and the cell sheet can be more efficiently produced. By culturing cells at a low-oxygen concentration, an extracellular matrix, specifically a cartilage-specific matrix is more efficiently synthesized, and the production of humoral factors and/or proteins contributing to repair of a cartilage tissue or a bone tissue can be promoted.

The cell sheet produced by the production method of the present invention can be released from the pore membrane by the following procedure, for example:
(1) the temperature of the culture medium is set at not less than an upper critical solution temperature or at not more than a lower critical solution temperature;
(2) a supporting membrane as a carrier is superimposed on the cell sheet, and the supporting membrane is preferably allowed to be in close contact with the cell sheet; and
(3) the cell sheet with the carrier is released from the pore membrane.

By releasing the cell sheet together with the carrier from the pore membrane, the cell sheet can be maintained so as not to shrink at the time of releasing. The carrier may be a polymer membrane, a structure molded from a polymer membrane, or a metal device, for example. Examples of the material of the carrier include hyaluronic acid, collagen, gelatin, fibrin, platelet-rich plasma, cellulose, other polysaccharides, polymers of biological origin such as protein, polyvinyl alcohol, polyvinylpyrrolidone, polyethylene glycol, polyvinylidene difluoride (PVDF), polypropylene, polyethylene, cellulose and derivatives thereof, paper, chitin, chitosan, and urethane.

The carrier may be preferably a PVDF sheet and more preferably a circular PVDF sheet having a hole at the center. By superimposing the PVDF sheet on the cell sheet and releasing the PVDF sheet together with the cell sheet from the pore membrane, the cell sheet can be more easily released from the pore membrane. In addition, by transplanting the cell sheet together with the PVDF sheet to an affected area, the cell sheet can be prevented from shrinking or breaking.

The carrier may be applied together with the cell sheet to an affected area. Next, the carrier can be released from the cell sheet by, for example, allowing the carrier to get wet to reduce the adhesion between the carrier and the cell sheet. The cell sheet is then appropriately cut by a surgical knife, scissors, laser light, plasma waves, or other means, as needed.

For example, when the circular PVDF sheet having a hole at the center is used as the carrier, and a cell sheet with the PVDF sheet is applied to an affected area and then is cut by, for example, laser light, the cell sheet can be prevented from adhering to areas other than the affected area.

The cell sheet produced by the production method of the present invention can be released not only by the release method using the carrier, but also by a release method without a carrier. The release method without a carrier can be the following method, for example: the pore membrane of a cell culture insert is detached by a surgical knife or the like, and is placed on a transplant device for an affected area. The release method is not limited to the method.

The present invention will next be described in further detail with reference to examples, but the invention is not intended to be limited to the examples.

Example 1

Introduction

Articular cartilage regeneration attracts particular attention in orthopedic studies. We have developed chondrocyte sheets for the regeneration of articular cartilage in knee osteoarthritis by using cell sheet engineering, and confirmed the safety and efficacy of self-derived chondrocyte sheets in clinical trials from 2011 to 2014. In ongoing clinical trials, we are preparing human transplantation of allogeneic chondrocyte sheets produced from polydactyly-derived chondrocytes (PDCs). As a preclinical model for evaluation of such chondrocytes, we reported the applicability of a rabbit xenotransplantation model to direct evaluation of human chondrocyte sheets (Takahashi, T. et al. Poster presentation: ORS Annual Meeting 2016). In the present study, we have used the model to evaluate PDC sheets produced in various culture conditions.

(Method)

Experiments were performed under approval and guidance by the institutional animal care and use committee and the independent ethics committee of Tokai University and after obtaining informed consent from patients. Chondrocytes were obtained from a patient (male, 8-month-old) underwent polydactyly surgery in Tokai University Hospital. PDCs were subcultured twice and then were cryopreserved. About 3 weeks before transplantation, the PDCs were thawed, then subcultured once, and seeded on temperature-responsive culture inserts at $1 \times 10^4$ cells/cm$^2$. The inserts were placed on a cell culture insert companion plate, then a culture medium was placed at the inside of the insert and the outside of the insert (the companion plate side), and consequently both the upper surface and the lower surface of the pore membrane were in contact with the culture medium. The inserts were produced by applying a temperature-responsive polymer onto the surface of a commercially available culture insert. The PDCs were cultured in the inserts for 2 weeks under the following conditions: group A (20% FBS in DMEM/F12); group B (20% by volume of FBS in DMEM/F12, containing transforming growth factor (TGF) β1 at a concentration of 10 ng/ml); and group C (20% FBS in DMEM/F12, containing TGF-β1 at a concentration of 10 ng/ml, 0.2% insulin-transferrin-selenium (41400-045, Life technologies), 1 mM pyruvic acid, 0.35 mM proline, and 0.1 μM dexamethasone). The culturing gave cell sheets. The sheets were evaluated by cell count, ELISA (enzyme-linked immunosorbent assay) (to determine production of TGF β1 and melanoma inhibitory activity (MIA) in 1% FBS for 72 hours), and histological analyses (safranin O staining and immunostaining for aggrecan, fibronectin, type I collagen, and type II collagen). Whether a sheet was positive or negative in such staining test was determined by a person skilled in the art. The antibodies against aggrecan used were, as the primary antibody, Aggrecan, G1-IGD-G2 Domain, Human, Recombinant, Carrier-free (R&D Systems, Inc., 1220-PG-025) and, as the secondary antibody, Donkey anti-Goat IgG(H+L) Cross-Adsorbed Secondary Antibody, Alexa Fluor 546 (Thermo Fisher Scientific Inc., A-11056). The antibodies against fibronectin used were, as the primary antibody, Anti-Fibronectin Antibody, cellular, clone DH1 (Merck, Ltd., MAB1940) and, as the secondary antibody, F(ab')2-Goat anti-Mouse IgG(H+L) Cross-Adsorbed Secondary Antibody, Alexa Fluor 488 (Thermo Fisher Scientific Inc., A-11017). The antibodies against type I collagen used were, for cell sheet staining, Goat Anti-Type I Collagen-UNLB (Southern Biotechnology Associates Inc., 1310-01) and, for transplant site staining, ImmPRESS (trademark) Reagent Anti-Goat Ig (Vector Laboratories, Inc., MP-7405). The antibody against type II collagen used was, for cell sheet staining, Anti-Human Type II Collagen (Kyowa Pharma Chemical Co., Ltd., F-57). The histological analysis was performed according to the following procedure in detail.

(Preparation Method of Frozen Sections to be Subjected to Histological Analysis)

Figure 1:
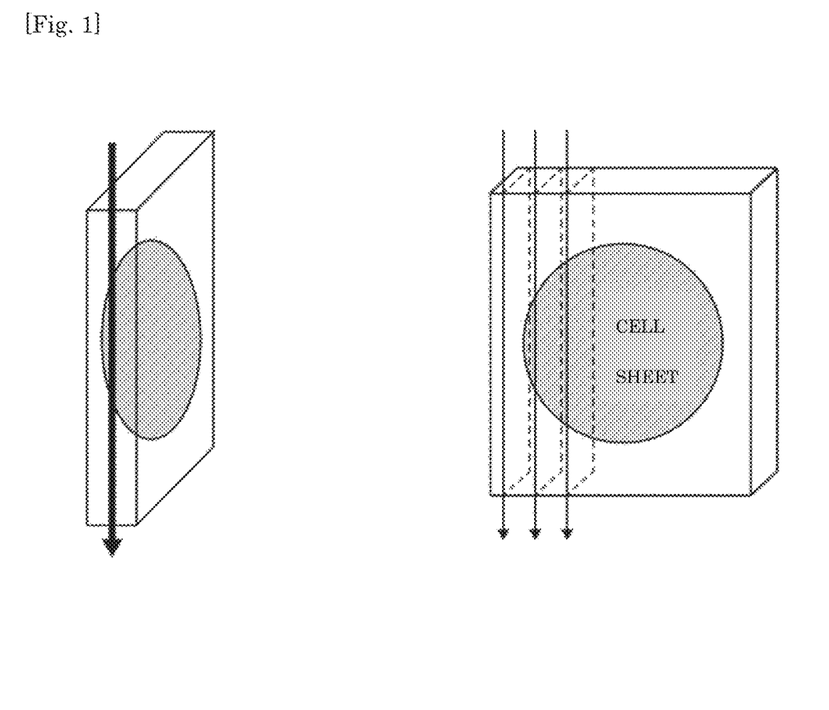
FIG. 1 shows views showing a slicing direction of a section.

A cell sheet was embedded in TISSUE-TEK™ O.C.T. compound (4583 Sakura Finetek Japan Co., Ltd.), and frozen sections were prepared. The frozen sections of the cell sheet were prepared by slicing the sheet perpendicular to the surface that had been in contact with the temperature-responsive culture dish as shown in FIG. 1. In FIG. 1, arrow directions are the slicing direction, and dotted lines indicate cut planes. A sliced section for immunostaining had a thickness of 20 μm, and a sliced section for staining except the immunostaining had a thickness of 10 μm. A sliced frozen section was placed on a slide glass, then immobilized with 4% PFA/PBS at room temperature for 10 minutes, and stained as described below.

(Preparation of Reagent)

The reagents used in histological analyses were prepared according to the following procedure.

Aqueous hematoxylin solution: Ion-exchanged water is placed in a flask and boiled. To the boiled ion-exchanged water, 1.5 g of hematoxylin (product number: 1.15938, manufacturer: MERCK) is added, and the hematoxylin is dissolved with a stirrer. While stirring, the solution is cooled to room temperature. To the solution, acetic acid (017-00256, Wako Pure Chemical Industries, Ltd.) is added to adjust the pH to 3.0. To the solution, 0.3 g of sodium iodate (190-02252, Wako Pure Chemical Industries, Ltd.) is added and stirred, and then 75 g of ammonium alum (018-01825, Wako Pure Chemical Industries, Ltd.) is added and stirred. After stirring, ion-exchanged water is added to make 1 L of a solution, and the solution is filtered to give an aqueous hematoxylin solution.

Eosin solution: First, 30 mL of pure eosin liquid (3204-2, Muto Pure Chemicals Co., Ltd.) and 120 mL of 95% ethanol are mixed to give an eosin solution. When used for staining, the eosin solution is diluted 5 times with 95% ethanol, and the diluted solution is used as an eosin solution.

Aqueous fast green solution: In 100 mL of ion-exchanged water, 80 mg of Fast Green (1A304, CHROMA) is dissolved, and the solution is filtered to give 0.08% by mass aqueous fast green solution.

Aqueous safranin O solution: In 100 mL of ion-exchanged water, 100 mg of Safranine O (1B463, CHROMA) is dissolved to give 0.1% by mass aqueous safranin O solution.

Citrate buffer solution: Citric acid monohydrate is dissolved in ion-exchanged water to give 0.01 M aqueous citric acid solution (hereinafter referred to as solution A). Trisodium citrate dihydrate is dissolved in ion-exchanged water to give 0.1 M aqueous sodium citrate solution (hereinafter referred to as solution B). Next, 95 mL of solution A and 415 mL of solution B are mixed and stirred, and 1N NaOH was used to adjust the pH to 6.0, giving 0.01 M citrate buffer solution.

(Safranin O Staining of Cell Sheet)

1. Pretreatment

The section was immersed in 100% ethanol for 10 minutes once.

2. Water Washing Treatment

The section treated in step 1 was washed with water.

3. Immersion in Ion-Exchanged Water

After the water washing in step 2, the section was immersed in ion-exchanged water for 5 minutes.

4. Hematoxylin Treatment

After the immersion in step 3, the section was immersed in the aqueous hematoxylin solution for 4 to 5 seconds.

5. Water Washing Treatment

After the treatment in step 4, the section was washed with warm water (50° C.) for 3 to 4 minutes.

6. Fast Green Treatment

After the washing in step 5, the section was immersed in the 0.08% by mass aqueous fast green solution for 10 minutes.

7. Acetic Acid Treatment

After the treatment in step 6, the section was treated with 1% by volume aqueous acetic acid solution once or twice.

8. Safranin Treatment

After the treatment in step 7, the section was immersed in the 0.1% by mass aqueous safranin O solution for 10 minutes.

9. Dehydration

After the treatment in step 8, the section was dehydrated by using an ethanol line. The ethanol line included seven portions of 100% by volume ethanol.

10. Clarification

After the dehydration in step 9, the section was clarified by using a xylene line. In other words, seven containers containing xylene were prepared, and the section was immersed in the xylene in each container.

11. Mounting

After the clarification in step 10, the section was mounted. For the mounting, Malinol (product number: 2009-3, manufacturer: Muto Pure Chemicals Co., Ltd.) was used as a mounting agent.

(Aggrecan Staining of Cell Sheet)

Aggrecan staining was performed by the same procedure as in the "Type I collagen staining of cell sheet" below except that the reagents used in "10. Primary antibody reaction" and "12. Secondary antibody reaction" were changed. The antibody used in the primary antibody reaction was Goat anti-human-aggrecan (SC006, R&D, diluted to 10 mg/mL with BlockAid™ Blocking Solution (Thermo Fisher Scientific Inc., Catalog no. B10710)). The reagent used in the secondary antibody reaction was Donkey anti-Goat IgG(H+L) Cross-Adsorbed Secondary Antibody, Alexa Fluor 546 (Thermo Fisher Scientific Inc., A-11056).

(Fibronectin Staining of Cell Sheet)

Fibronectin staining was performed by the same procedure as in the "Type I collagen staining of cell sheet" below except that the reagents used in "10. Primary antibody reaction" and "12. Secondary antibody reaction" were changed. The antibody used in the primary antibody reaction was Anti-Fibronectin mIgG (MAB1940, Chemicon, diluted to 0.2 µg/mL with 1% Goat Normal Serum). The reagent used in the secondary antibody reaction was F(ab')2-Goat anti-Mouse IgG(H+L) Cross-Adsorbed Secondary Antibody, Alexa Fluor 488 (Thermo Fisher Scientific Inc., A-11017).

(Type I Collagen Staining of Cell Sheet)

1. Pretreatment

A section was immersed in 100% ethanol for 5 minutes three times. Next, the section was immersed in 70% ethanol for 5 minutes once.

2. Water Washing Treatment

The section treated in step 1 was washed with water.

3. Immersion in Ion-Exchanged Water

After the water washing in step 2, the section was immersed in ion-exchanged water for 5 minutes.

4. Antigen Activation Treatment

After the immersion in step 3, the section was immersed in the citrate buffer solution at 98° C. for 10 minutes.

5. Immersion in Ion-Exchanged Water

After the treatment in step 4, the section was immersed in ion-exchanged water for 5 minutes three times.

6. Immersion in Methanol Solution Containing Hydrogen Peroxide

After the immersion in step 5, the section was immersed in a methanol solution containing hydrogen peroxide (0.3% by mass $H_2O_2$) for 15 minutes.

7. Immersion in Ion-Exchanged Water

After the immersion in step 6, the section was immersed in ion-exchanged water for 5 minutes three times.

8. PBS Washing

After the immersion in step 7, the section was immersed in 0.01 M PBS for 5 minutes three times.

9. Blocking by Serum

After the washing in step 8, the section was immersed in 2.5% normal horse serum (serum attached to ImmPRESS HRP REAGENT KIT Anti-GOAT IgG (#MP-7405), VECTOR) for 10 minutes.

10. Primary Antibody Reaction

After the blocking in step 9, the section was subjected to primary antibody reaction using an antibody against type I collagen (1310-01, SouthernBiotech, 1:100 dilution with 0.01 M PBS) for 2 hours.

11. PBS Washing

After the reaction in step 10, the section was immersed in 0.01 M PBS for 5 minutes three times.

12. Secondary Antibody Reaction

After the washing in step 11, the section was subjected to secondary antibody reaction using ImmPRESS Polymer Anti-Goat IgG Reagent (MP-7405, Vector Laboratories) for 1 hour.

13. PBS Washing

After the reaction in step 12, the section was immersed in 0.01 M PBS for 5 minutes three times.

14. Coloring

After the washing in step 13, the section was subjected to coloring reaction using DAB (0.05 M Tris-HCl (200 ml), DAB (40 mg), and 30% $H_2O_2$ (34 µl)) for 2 minutes.

15. Immersion in Ion-Exchanged Water

After the coloring reaction in step 14, the section was immersed in ion-exchanged water for 5 minutes.

16. Nuclear Staining

After the immersion in step 15, the section was treated with the aqueous hematoxylin solution for 2 seconds.

17. Water Washing Treatment

After the treatment in step 16, the section was washed with water.

18. Dehydration, Clarification, and Mounting

These treatments were performed in the same manner as in the "Safranin O staining of cell sheet".

(Type II Collagen Staining of Cell Sheet)

Type II collagen staining was performed by the same procedure as in the "type I collagen staining of cell sheet" above except that the reagents used in "10. Primary antibody reaction" and "12. Secondary antibody reaction" were changed. The antibody used in the primary antibody reaction was type II collagen primary antibody (Kyowa Pharma Chemical Co., Ltd., 1:100 dilution with 0.01 M PBS). The reagent used in the secondary antibody reaction was ImmPRESS Polymer Anti-Mouse IgG Reagent (MP-7402, Vector Laboratories).

In the present study, 16 female Japanese white rabbits (average: 3.0 kg) were used. As reported previously (Ito, S. et al., Biomaterials 2012), a cartilage defect was made in the patella groove of the femoral in the right knee of each rabbit in a diameter direction of 5 mm and a depth direction of 3 mm, and the flow out of bone marrow from the subchondral bone was confirmed. The rabbits were randomly assigned to treatment groups (n=4 in each group). In groups A, B, and C, a single PDC sheet was transplanted to a knee, and in group D, no treatment was performed. The rabbits were immunosuppressed by tacrolimus (Astellas Pharma Inc.) for 4 weeks and were sacrificed 4 weeks after the transplantation. Cartilage repair was histologically evaluated by staining (hematoxylin and eosin, and safranin O) and immunostaining (type I collagen, type II collagen, and human-specific vimentin). The sections stained with safranin O were graded by two skilled orthopedists in accordance with the modified grading system (a maximum of 45 points) by International Cartilage Repair Society (ICRS). Sections were also graded in terms of expression of type I collagen and type II collagen in a whole repair tissue and in a region having a human-derived tissue, using a 100-point scale. One-way analysis of variance by Tukey's post test was used to compare the points between groups. A preparation method and a staining method of the sections subjected to these evaluations are as described below.

(Preparation Method of Section)

A cartilage part was immobilized and then was embedded in paraffin. The immobilization was performed by immersion in 20% formalin. The embedding was performed with an embedding agent, Histoprep 586 (415-25791, Wako Pure Chemical Industries, Ltd.) by using an embedding console system (TISSUE-TEK™, Sakura Finetek Japan Co., Ltd.). The embedded sample was placed in upright position and was sliced in the vertical direction. A sliced section for immunostaining had a thickness of 20 μm, and a sliced section for staining except the immunostaining had a thickness of 10 μm. A sliced section was placed on a slide glass and stained as described below.

(Hematoxylin and Eosin Staining of Cartilage)

1. Deparaffinization Treatment

A section was immersed in xylene for 5 minutes three times. Then, the section was immersed in 100% ethanol for 5 minutes three times. Next, the section was immersed in 70% ethanol for 5 minutes once.

2. Water Washing Treatment

After the treatment in step 1, the section was washed with water.

3. Immersion in Ion-Exchanged Water

After the water washing in step 2, the section was immersed in ion-exchanged water for 5 minutes.

4. Hematoxylin Treatment

After the immersion in step 3, the section was immersed in the aqueous hematoxylin solution for 3 to 4 minutes.

5. Water Washing Treatment

After the treatment in step 4, the section was washed with warm water (50° C.) for 3 to 4 minutes.

6. Eosin Treatment

After the washing in step 5, the section was immersed in the eosin solution for 10 minutes.

7. Dehydration, Clarification, and Mounting

These treatments were performed in the same manner as in the "Safranin O staining of cell sheet".

(Safranin O Staining of Cartilage)

Staining was performed according to the same procedure as in the "Safranin O staining of cell sheet" except that "1. Deparaffinization treatment" described in the "Hematoxylin and eosin staining of cartilage" was performed in place of "1. Pretreatment" in the "Safranin O staining of cell sheet".

(Type I Collagen Staining of Cartilage)

Staining was performed according to the same procedure as in the "Type I collagen staining of cell sheet" except that "1. Deparaffinization treatment" described in the "Hema-toxylin and eosin staining of cartilage" was performed in place of "1. Pretreatment" in the "type I collagen staining of cell sheet".

(Type II Collagen Staining of Cartilage)

Staining was performed by the same procedure as in the "Type II collagen staining of cell sheet" except that "1. Deparaffinization treatment" described in the "Hematoxylin and eosin staining of cartilage" was performed in place of "1. Pretreatment" in the "type II collagen staining of cell sheet".

(hVimentin Staining of Cartilage)

1. Deparaffinization Treatment

Deparaffinization treatment was performed in the same manner as described in the "Hematoxylin and eosin staining".

2. Water Washing Treatment

After the deparaffinization treatment in step 1, the section was washed with water.

3. Immersion in Ion-Exchanged Water

After the water washing in step 2, the section was immersed in ion-exchanged water for 5 minutes.

4. Antigen Activation

After the immersion in step 3, the section was immersed in the citrate buffer solution at 98° C. for 10 minutes.

5. Cooling

After the treatment in step 4, the section was cooled on a laboratory table for 30 minutes.

6. Blocking by Serum

After the cooling in step 5, the section was treated with 0.01 M PBS (containing 0.2% Tween) containing 5% normal goat serum (product number: D204-00-0100, manufacturer: ROCKLAND) for 1 hour.

7. Antibody Reaction

After the blocking in step 6, the section was subjected to antibody reaction using anti-human Vimentin antibody Alexa Fluor 647 Conjugate (#9856, CST, 1:100 dilution with 0.01 M PBS) at 4° C. for 16 hours.

8. PBS Washing

After the reaction in step 7, the section was immersed in 0.01 M PBS for 5 minutes three times.

9. Mounting

After the washing in step 8, the section was mounted with VECTASHIELD HardSet Antifade Mounting Medium with DAPI (Vector Laboratories).

(Results)

In-vitro features of PDC sheets prepared in various culture conditions are summarized in Table 1.

TABLE 1

Overview of in-vitro features of PDC sheet

| Group | A | B | C |
|---|---|---|---|
| Cell number per sheet ($\times 10^6$ cells) | 2.8 ± 0.7 | 1.1 ± 0.6 | 1.0 ± 0.3 |
| TGF-β1 production (ng/ml) | 1.8 ± 0.4 | 0.9 ± 0.2 | 3.6 ± 0.3 |
| MIA production (ng/ml) | 16.7 ± 7.4 | 1.6 ± 0.5 | 7.3 ± 3.5 |
| Sheet thickness (μm) | 16.4 ± 2.2 | 14.9 ± 4.4 | 31.6 ± 5.7 |
| Safranin O staining | Negative | Negative | Negative |
| Aggrecan | Positive | Positive | Positive |
| Fibronectin | Positive | Positive | Positive |
| Type I collagen | Positive | Positive | Positive |
| Type II collagen | Negative | Negative | Negative |

* Each numerical value is an average ± standard error.

As shown in Table 1, the cell number per sheet was significantly higher in group A than in group B ($p<0.01$) or group C ($p<0.01$). The TGF β1 production significantly differed among all three groups (A vs. B, $p<0.05$; A vs. C, p<0.01; B vs. C, p<0.01), and was highest in group C and lowest in group B. The MIA production was significantly higher in group A than in group B (p<0.01) or group C (p<0.05). The sheet thickness was significantly more in group C than in group A (p<0.01) or group B (p<0.01). Sheets in each group were stained with aggrecan, fibronectin, and type I collagen, but were not stained with safranin O or type II collagen.

Figure 2:
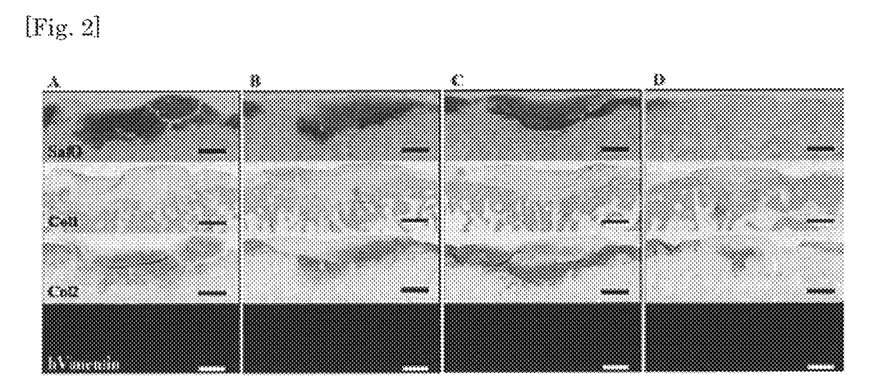
FIG. 2A shows photographs of a repaired tissue of Group A.
FIG. 2B shows photographs of a repaired tissue of Group B.
FIG. 2C shows photographs of a repaired tissue of Group C.
FIG. 2D shows photographs of a not repaired tissue of Group D.

Histological evaluations of repaired tissues 4 weeks after transplantation are summarized in Table 2 and FIG. 2.

TABLE 2

Overview of histological evaluations of repaired tissue transplanted with PDC sheet

| Group | A | B | C | D |
|---|---|---|---|---|
| ICRS score (of 45 points) | 34.5 ± 1.4 | 30.1 ± 1.4 | 32.5 ± 2.8 | 22.1 ± 1.8 |
| Safranin O in human tissue (of 100 points) | 87.0 ± 3.5 | 38.0 ± 9.0 | 65.3 ± 17.8 | N/A |
| Type I collagen in human tissue (of 100 points) | 17.3 ± 5.5 | 19.3 ± 4.7 | 41.8 ± 18.6 | N/A |
| Type II collagen in human tissue (of 100 points) | 67.3 ± 10.5 | 25.0 ± 8.4 | 12.0 ± 2.7 | N/A |
| Ratio of type II collagen and type I collagen in human tissue | 3.9 ± 1.4 | 1.3 ± 0.5 | 0.3 ± 0.1 | N/A |

* Each numerical value is an average ± standard error.

As shown in Table 2, the ICRS score was significantly higher in groups A, B, and C than in group D (A or C vs. D, p<0.01; B vs. D, p<0.05). The type II collagen in the human tissue was significantly higher in group A than in group B (p<0.05) or group C (p<0.01). The ratio of type II collagen and type I collagen in the human tissue was significantly higher in group A than in group C (p<0.05).

As seen in the above results, a cell sheet that is formed from a culture of cells derived from a cartilage tissue and is negative for immunostaining using an antibody against type II collagen has a cartilage repair function.

The invention claimed is:

1. A method for producing a cell sheet for cartilage repair, the cell sheet being formed from a culture of cells derived from a cartilage tissue, the method comprising:
    culturing cells derived from a cartilage tissue on a surface of a membrane, a temperature-responsive polymer being immobilized on the surface, to produce a cell sheet of cultured cells, and
    evaluating the cell sheet of cultured cells as a cell sheet suitable for cartilage repair, when the cell sheet of the cultured cells shows positive in immunostaining using an antibody against type 1 collagen and negative in immunostaining using an antibody against type 2 collagen,
    wherein the culturing is stopped before the cell sheet of cultured cells evaluated as the cell sheet suitable for cartilage repair becomes positive for immunostaining using an antibody against type II collagen.

2. The production method according to claim 1, wherein the cell sheet is positive for immunostaining using an antibody against type I collagen when the culturing is stopped.

3. The production method according to 1, wherein the culturing is continued until the cell sheet becomes positive for immunostaining using an antibody against aggrecan.

4. The production method according to claim 1, wherein the culturing is stopped before the cell sheet becomes positive for safranin O staining.

5. The production method according to claim 1, wherein an amount of the polymer immobilized on the surface is 0.3 to 5.0 µg/cm$^2$.

6. The production method according to claim 5, wherein the membrane is a pore membrane, and during the culturing, the cells are in contact with a culture medium on an upper side of the pore membrane and in contact with a culture medium on a lower side of the pore membrane through pores in the pore membrane.

7. The production method according to claim 1, wherein the membrane is a pore membrane, and in the culturing, the cells are in contact with a culture medium on an upper side of the pore membrane and in contact with a culture medium on a lower side of the pore membrane through pores in the pore membrane.

8. The production method according to claim 1, wherein the culturing is performed by using a cell culture insert.

9. The production method according to claim 1, wherein the culturing is conducted for 10 to 20 days.

10. The production method according to claim 1, wherein the culturing is conducted for 12 to 16 days.

11. The production method according to claim 1, wherein said temperature-responsive polymer immobilized on the membrane surface is poly(N-isopropylacrylamide).

12. The production method according to claim 1, wherein said cells are polydactyly-derived chondrocytes (PDCs).

13. The production method according to claim 12, wherein said PDCs are seeded onto said membrane in an amount of 1×10$^4$ cells/cm$^2$.

14. The production method according to claim 12, wherein said PDCs are cultured in 20% fetal bovine serum (FBS) in Dulbecco's Modified Eagle Medium: Nutrient Mixture F-12 (DMEM/F12).

15. The production method according to claim 12, wherein the cell sheet does not comprise cells derived from a synovial membrane.

16. A method for producing a cell sheet for cartilage repair, the cell sheet being formed from a culture of cells derived from a cartilage tissue, the method comprising:
    culturing for 12 to 16 days cells derived from a cartilage tissue on a surface of a membrane, a temperature-responsive polymer comprising poly(N-isopropylacrylamide) being immobilized on the surface, to produce the cell sheet;
    and evaluating the cell sheet of cultured cells as a cell sheet suitable for cartilage repair, when the cell sheet of cultured cells shows positive in immunostaining using an antibody against type 1 collagen and negative in immunostaining using an antibody against type 2 collagen,
    wherein the culturing is stopped before the cell sheet of cultured cells evaluated as the cell sheet suitable for cartilage repair becomes positive for immunostaining using an antibody against type II collagen;
    and wherein the membrane is a pore membrane, and during culturing, the cells are in contact with a culture medium on an upper side of the pore membrane and in contact with a culture medium on a lower side of the pore membrane through pores in the pore membrane.

17. The production method according to claim 16, wherein said cells are polydactyly-derived chondrocytes (PDCs).

18. The production method according to claim 17, wherein the cell sheet does not comprise cells derived from a synovial membrane.

19. The production method according to claim 16, wherein the cell sheet does not comprise cells derived from a synovial membrane.

\* \* \* \* \*